United States Patent
Armanino (10) Patent No.: US 8,932,055 B2
(45) Date of Patent: Jan. 13, 2015

(54) METHOD EMPLOYING ELECTRIC FIELDS TO SELECTIVELY KILL MICROBES IN A ROOT CANAL PREPARATION

(75) Inventor: Roberto Armanino, Genoa (IT)

(73) Assignee: Roberto Armanino, Genoa (IT)

( * ) Notice: Subject to any disclaimer, the term of this patent is extended or adjusted under 35 U.S.C. 154(b) by 48 days.

(21) Appl. No.: 12/813,565

(22) Filed: Jun. 11, 2010

(65) Prior Publication Data

US 2011/0039226 A1 Feb. 17, 2011

Related U.S. Application Data

(60) Provisional application No. 61/232,920, filed on Aug. 11, 2009, provisional application No. 61/174,562, filed on Jun. 11, 2009.

(51) Int. Cl.
A61C 3/00 (2006.01)

(52) U.S. Cl.
USPC .............................. 433/32; 433/224

(58) Field of Classification Search
USPC ............ 433/32, 224, 29, 102; 604/20, 41, 44, 604/46, 48, 49
See application file for complete search history.

(56) References Cited

U.S. PATENT DOCUMENTS

| | | | |
|---|---|---|---|
| 1,713,971 A * | 5/1929 | Lowry et al. ..................... 606/49 |
| 4,175,565 A | 11/1979 | Chiarenza et al. | |
| 4,243,388 A * | 1/1981 | Arai ................................ 433/27 |
| 4,291,125 A * | 9/1981 | Greatbatch .................... 424/618 |
| 4,854,865 A | 8/1989 | Beard et al. | |
| 5,383,935 A | 1/1995 | Shirkhanzadeh | |
| 5,421,727 A * | 6/1995 | Stevens et al. ................ 433/224 |
| 5,462,644 A * | 10/1995 | Woodson ...................... 205/701 |
| 5,725,377 A | 3/1998 | Lemler et al. | |
| 6,273,720 B1 | 8/2001 | Spalten | |
| 6,413,498 B1 | 7/2002 | Malmagro | |
| 6,419,642 B1 * | 7/2002 | Marchitto et al. ............ 600/573 |
| 6,482,008 B2 * | 11/2002 | Perdomini et al. ............ 433/224 |
| 6,482,309 B1 | 11/2002 | Green et al. | |
| 6,555,055 B1 | 4/2003 | Cisar et al. | |
| 6,593,130 B1 * | 7/2003 | Sen et al. .................... 435/285.2 |
| 6,641,396 B2 * | 11/2003 | Pasquantonio et al. ..... 433/217.1 |
| 6,778,861 B1 | 8/2004 | Liebrecht et al. | |
| 2002/0090594 A1 * | 7/2002 | Riitano et al. ................ 433/224 |

(Continued)

OTHER PUBLICATIONS

Valle et al, "A new theaputic protocal for paediatric endodontics: a case report", Sep. 2005, ctsocumoo GIII£ml0- val. 19- II. 2, pp. 210-213, see http://www.d-p-s.uk.com/comfort-zone/downloads/Endox%20Rome%20Paper.pdf.*

(Continued)

*Primary Examiner* — Heidi M Eide
*Assistant Examiner* — Matthew Saunders
(74) *Attorney, Agent, or Firm* — Workman Nydegger (57) ABSTRACT

Methods employing an electric field for disinfection of a root canal preparation during an endodontic procedure. A monopolar electrode probe sized and configured for insertion into a root canal of a tooth is inserted within the root canal preparation. A ground electrode is electrically connected to the patient to complete the circuit with the monopolar electrode probe. An electrical voltage is applied between the probe and ground, resulting in virtually no current flow between the electrodes, but rather the generation of an electric field within the root canal and adjacent dental tissues. The electric field kills microbes within the root canal system of the tooth without significant heating or damage to surrounding dental tissue.

35 Claims, 4 Drawing Sheets

(56) References Cited

U.S. PATENT DOCUMENTS

| | | |
|---|---|---|
| 2003/0060856 A1* | 3/2003 | Chornenky et al. ............ 607/40 |
| 2004/0034395 A1 | 2/2004 | Dick |
| 2004/0059285 A1* | 3/2004 | Mathiesen et al. ............ 604/65 |
| 2004/0101809 A1* | 5/2004 | Weiss et al. ................... 433/224 |
| 2006/0144718 A1 | 7/2006 | Lambie |
| 2006/0265026 A1 | 11/2006 | Madjar et al. |
| 2006/0286511 A1* | 12/2006 | Aleksandrovskiy et al. . 433/215 |
| 2006/0293724 A1 | 12/2006 | Kronberg et al. |
| 2007/0105799 A1* | 5/2007 | Hermanson .................... 514/44 |
| 2008/0199830 A1* | 8/2008 | Fontenot et al. ............. 433/215 |
| 2009/0326436 A1* | 12/2009 | Rubinsky et al. ............... 604/20 |
| 2010/0047735 A1* | 2/2010 | Pond .............................. 433/29 |

OTHER PUBLICATIONS

Valle et al, "A new theraputic protocol for paediatric endodontics:a case report", Sep. 2005, ctsocumoo G It Endo-vol. 19-n.3,pp. 210-213, see http://www.d-p-s.uk.com/comfort-zone/downloads/Endox%20ROME%20 papaer.pdf.*

* cited by examiner

METHOD EMPLOYING ELECTRIC FIELDS TO SELECTIVELY KILL MICROBES IN A ROOT CANAL PREPARATION

CROSS REFERENCE TO RELATED APPLICATION

This application claims the benefit of earlier filed U.S. Provisional Application No. 61/174,562, filed Jun. 11, 2009, and also U.S. Provisional Application No. 61/232,920, filed Aug. 11, 2009, the disclosures of which are incorporated herein in their entirety.

BACKGROUND OF THE INVENTION

1. The Field of the Invention

The present invention relates to procedures for preparing a root canal of a tooth for receiving a sealer and/or filler material. More particularly, the invention relates to methods for disinfecting a root canal prior to introduction of a sealer and/or filler material therein.

2. The Relevant Technology

When a root canal of a living tooth becomes infected or abscessed, discomfort and, in many cases, severe pain can result. In the early days of dentistry the only solution was to extract the tooth. More recently, however, dental practitioners have developed techniques to successfully remove the pulp material that forms the nerve of the tooth, which has become infected, and therefore save the teeth while preventing the spread of infection to the patient. After careful preparation of the canal that contained the infected nerve and other pulp material, the canal is refilled with an inert filling material, such as gutta percha, and/or a curable sealer or filler material. This process allows the patient to retain the tooth.

To achieve a successful root canal restoration, the dental practitioner must carefully, and as completely as possible, remove the infected pulp material. The pulp removal process typically includes shaping the root canal with one or more endodontic instruments so that it can be effectively and successfully filled and sealed with an inert material to reduce the possibility of further infection.

Cleaning and shaping the root canal in preparation for receiving a sealing and/or filling material is achieved by the use of metal endodontic instruments that include cutting surfaces for removing tissue in the root canal. Since root canals are seldom straight, often having bends and twists, at least some endodontic instruments are flexible so as to allow the instrument to follow the curvature of the root canal. Currently preferred materials of construction include stainless steel and super-elastic alloys, e.g., nickel-titanium (Ni—Ti) alloys.

In addition, even once the diseased pulp and nerve tissue have been removed, it is generally necessary to disinfect remaining surfaces and lateral canals of the root canal so as to kill existing bacteria, as well as to prevent later growth of bacteria and/or other microbes, which could lead to further degradation or even loss of the entire tooth. Typically, the practitioner chemically disinfects the root canal preparation, for example, by introducing aqueous sodium hypochlorite into the root canal, followed by rinsing the canal with pure water. Once disinfected and rinsed, the canal is dried prior to filling and sealing. Even with such chemical disinfection, there is still a risk that a significant bacterial population can remain and propagate over time (e.g., within lateral pores or canals that branch off the main root canal), thereby causing risk of further infect and pain to the patient. Improved disinfection techniques would be advantageous as they would reduce the frequency of or even eliminate sealed root canals later developing infection.

BRIEF SUMMARY OF THE PREFERRED EMBODIMENTS

The present invention is directed to a method for disinfecting a root canal preparation during an endodontic procedure. The disclosed methods generally involve the application of an electric field in a manner that kills any bacteria that may remain in a root canal after an endodontic procedure while minimizing heat and/or damage to surrounding dental tissue.

According to one embodiment, the apparatus employed during the disclosed procedures includes a monopolar electrode probe which is sized and configured for insertion into a root canal of a tooth (e.g., having a length of about 15 mm and a diameter of about 0.5 mm), a ground electrode that is electrically connectable to a patient, and a power source for providing an electrical voltage between the monopolar electrode probe and the ground electrode.

One exemplary method comprises the steps of: (1) electrically connecting the ground electrode to a patient so as to provide an electrical ground that will complete the circuit with the monopolar electrode probe; (2) inserting the monopolar electrode probe into a root canal preparation of a patient; and (3) applying an electrical voltage between the ground and the inserted probe so as to produce an electric field within the root canal preparation, between the probe and the periodontium, killing any microbes still present without significantly damaging or heating surrounding dental tissue (e.g., periodontium, alveolar bone, or adjacent dentin).

In 1942, Suzuki (Experimental Studies on Ionophoresis, J. Jpn. Stomatol. 16 (1942), pp. 411-417. 4 I) demonstrated that the periodontium of each tooth exhibits substantially identical resistance at any given location, calculated between it and, for example, a ground electrode attached to oral tissue or held in the patient's hand. In other words, the periodontium acts as an equipotential membrane surrounding the roots of a person's teeth. The resistance value was proposed by I. Sunada (New Method for Measuring the Length of the Root Canal, Journal of Dental Research 41 (1962), 375-87) and J. Dahlin (Electrometric Measuring of the Apical Foramen, A New Method for Diagnosis and Endodontic Therapy. Quintessence International 10, (1979), pp. 13-22).

As a result, it has now been discovered that by applying a voltage between the probe and the ground electrode (e.g., in the hand of the patient or attached to the gingiva), an electric field can be generated between the inner root canal system and the periodontium. Where the ground electrode is held in the patient's hand, the rest of the patient's body between the hand and the periodontium simply acts as a large electrical conductor. Since the electric field strength increases as the distance between the electrodes is reduced, and because of the relatively low conductivity of the dentin, it is believed that this is the reason why such an electric field can be generated without damage to surrounding tissue while still killing any microbes that may be present in the root canal.

Advantageously, the applied voltage is sufficiently low so that preferably virtually no electrical current flows between the ground and the electrode probe, but high enough to generate an electric field capable of eradicating the microbial population (e.g., through electroporation of the cell walls of the microbes and/or apoptosis). Virtually no current flow results in substantially no heating of surfaces or materials within the root canal (e.g., surrounding dental tissue is heated by less than about 10° C., or less than about 5° C., or less than about 2° C. or essentially no heating) only the generation of a disruptive electric field that is sufficient to selectively target and kill microbes without damaging surrounding dental tissue.

The inventive method provides for simple, effective, rapid and substantially complete disinfection of a root canal preparation, after which the practitioner may proceed to complete the endodontic procedure (e.g., drying, filling and sealing of the root canal).

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention is directed towards methods for disinfection of a root canal preparation during an endodontic procedure. The disclosed methods generally involve the application of an electric field in a manner that kills any bacteria that may remain in a root canal after an endodontic procedure while minimizing heat and/or damage to surrounding dental tissue.

According to one embodiment for carrying out the disclosed methods, a monopolar electrode probe sized and configured for insertion into a root canal of a tooth is inserted within the root canal preparation. A ground electrode is electrically connected to the patient (e.g., to the patient's hand). The ground is electrically connected to the monopolar electrode probe through the patient's body, and an electrical voltage is applied between the probe and the ground, resulting in virtually no current flow between the monopolar and ground electrodes, but still generating an electric field in the root canal and optionally surrounding dental tissue. The electric field kills microbes within the root canal of the tooth and optionally within adjacent dentin without significant heating or damaging surrounding dental tissues.

II. Exemplary Apparatus and Methods

Figure 1:
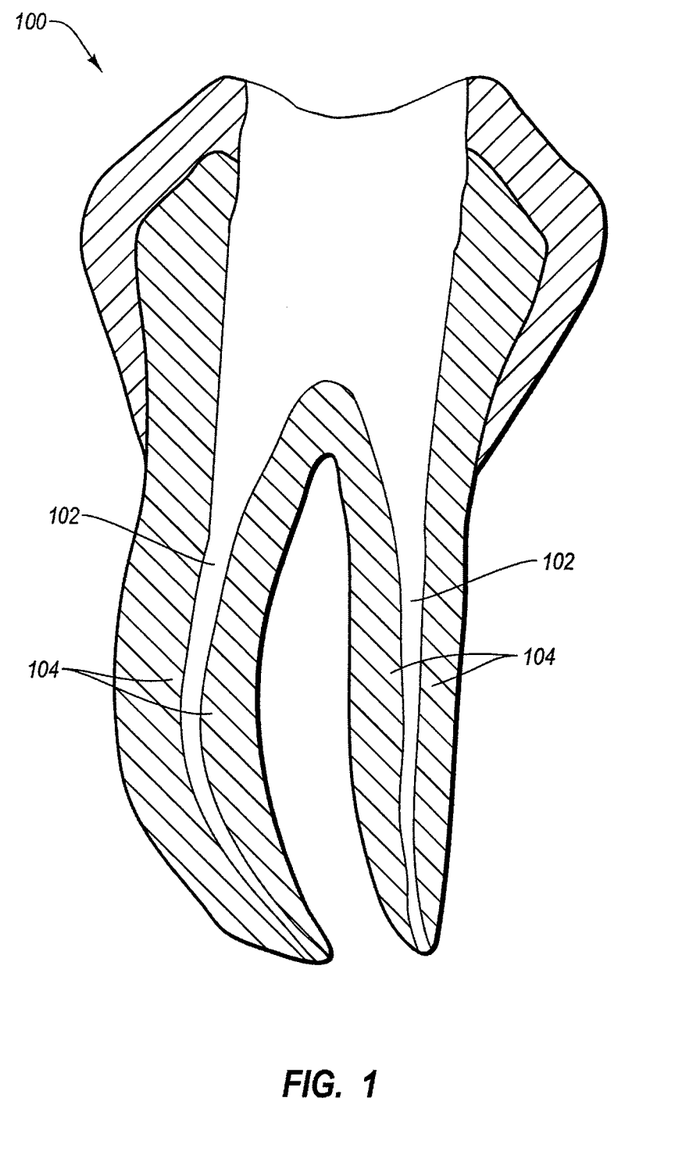
FIG. 1 illustrates a root canal preparation of a tooth in which the pulp and nerve tissue have been removed.

FIG. 1 illustrates a tooth 100 in which one or more root canals 102 of a tooth have been prepared by removing necrotic pulp and nerve material from root canal(s) 102 in preparation for filing and sealing of the root canal(s) 102. Bacteria and other microbes are typically present within root canal 102 and on adjacent dentin surfaces 104, both as a biofilm and in planktonic formats. Once the root canal 102 has been cleared of necrotic diseased nerve tissue and other relatively large debris particles, an aqueous wash may be introduced into root canal(s) 102 to aid in removal of any residual debris. Using state of the art methods, such a wash may comprise a chemical disinfecting wash solution (e.g., aqueous sodium hypochlorite) that is introduced into the root canal(s) 102 to aid in removal of any residual debris and optionally to disinfect the root canal. While such applications are helpful in eradicating a microbial population, the aqueous chemical disinfecting solution may often not completely kill bacteria and other microbes present within the root canal(s) 102, particularly due to the microanatomy of the dentin where lateral micro-fissures, cracks or other micro-channels may be present. The disinfecting wash solution may not, in all cases, be able to fully penetrate into all regions of the root canal(s), including lateral canals and fissures, where infection may be hiding. As a result, infection and microbes may continue to lurk even after diligent cleaning and disinfecting of the root canal(s).

As such, according to the present invention, methods of disclosed embodiments include a process by which bacteria and other microbes within the root canal(s) 102 are eradicated by generation of an electric field within the root canal 102. Although nothing forecloses their use in the context of the disclosed methods, it may be unnecessary to apply a chemical disinfecting wash in all cases, or even in any cases, although such a wash may be applied so as to provide chemical disinfection in conjunction with methods for disinfection using an electric field. Preferably, the root canal 102 is washed with an aqueous EDTA solution (e.g., 0.5 M EDTA) in order to open dentinal tubules by at least partially removing the smear layer plugs produced during cleaning and abrading of the root canal 102. The EDTA wash may be followed by a wash of water and/or an aqueous saline solution in preparation for the electric field disinfection. Depending on the total electrical resistance of the root canal system, the use of a saline solution may be advantageous, as it can provide ions within the liquid occupying the root canal $102(s)$ while applying an electric field, which is believed to aid in propagating and locally increasing the strength of the generated electric field within the root canal and associated dentinal tubules. Once the root canal 102 has been washed (and optionally disinfected using an antiseptic solution), it is ready for in vivo generation of the disinfecting electric field.

Figure 2:
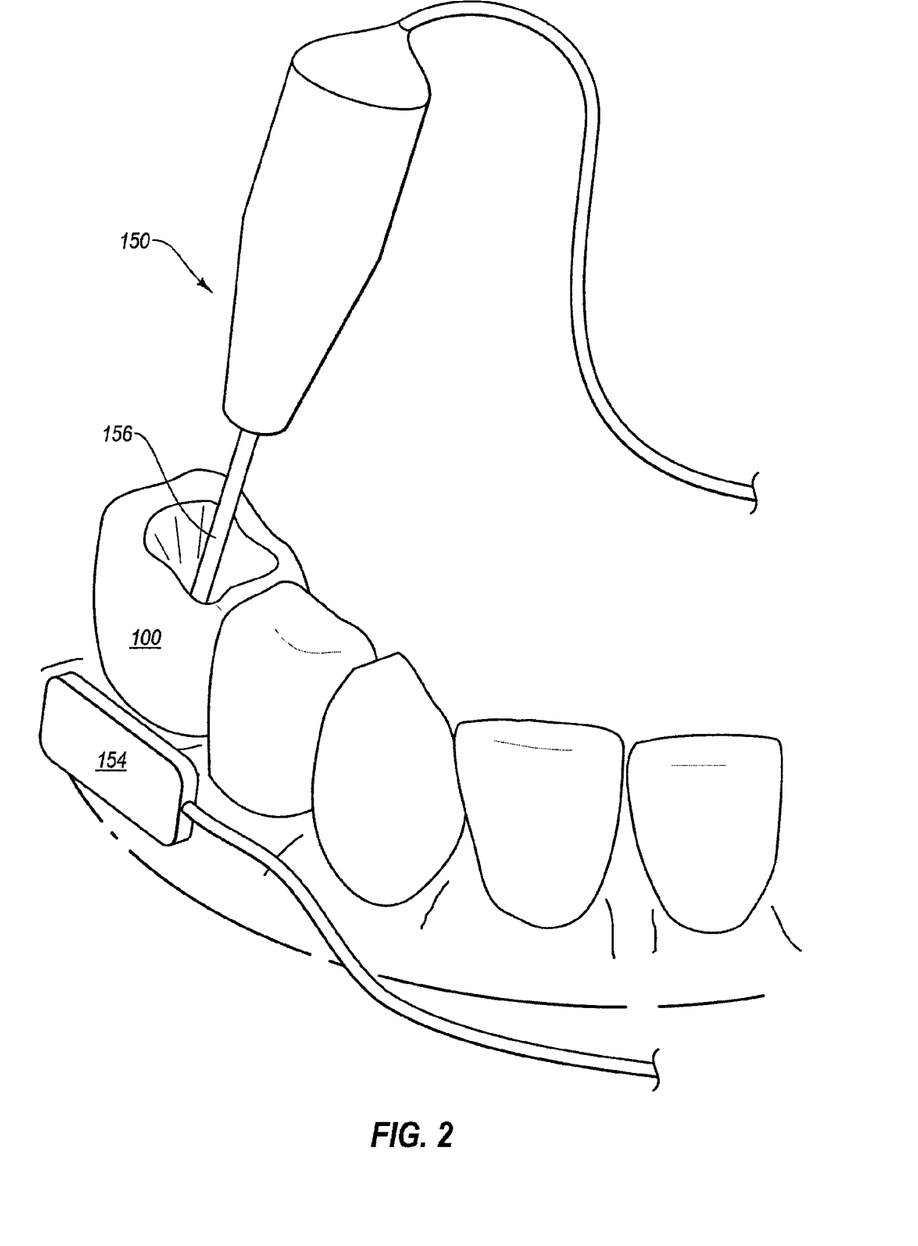
FIG. 2 is a perspective view of a patient's mouth in which the ground electrode is connected to the gingiva and the monopolar electrode probe is inserted by the practitioner within the root canal preparation of FIG. 1 while an electrical voltage potential is applied.
Figure 3:
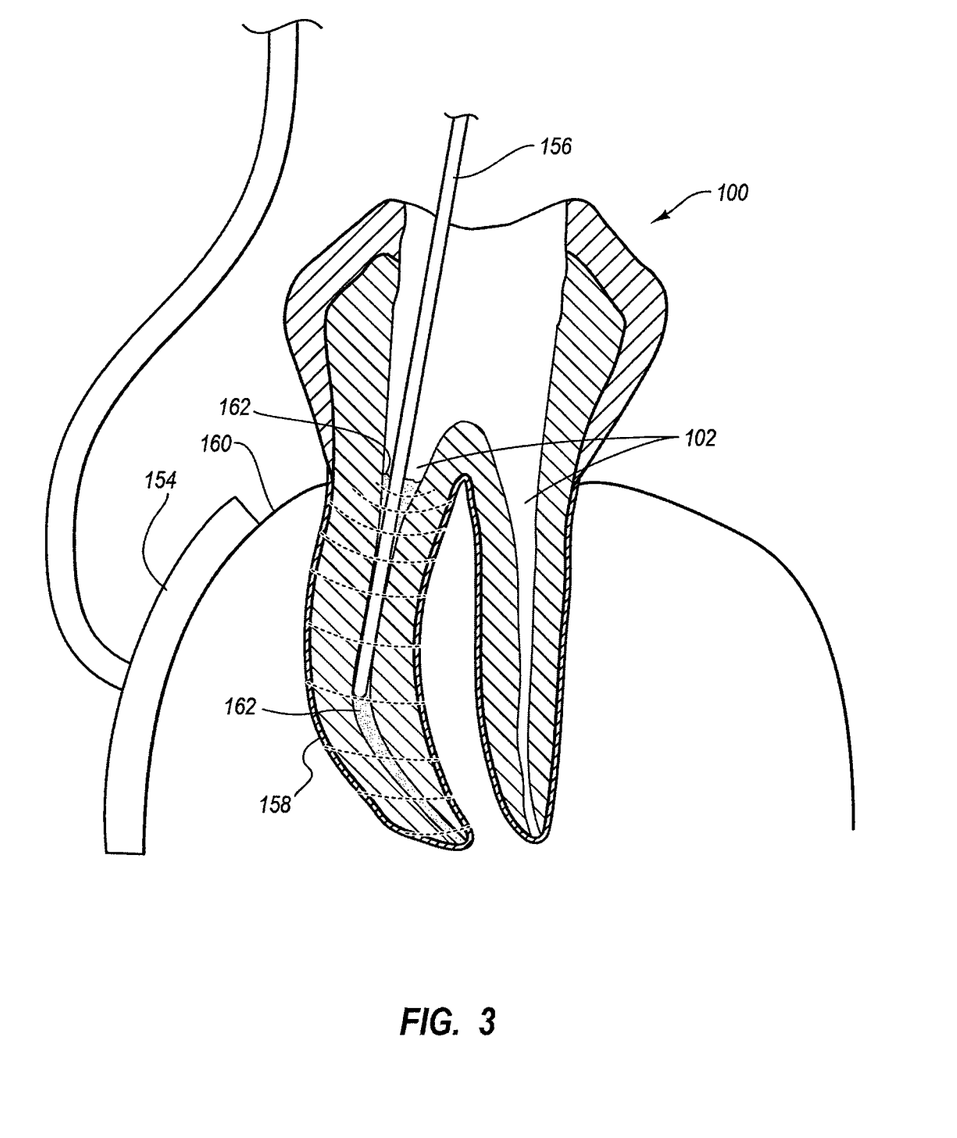
FIG. 3 is a close up cross-sectional view of the root canal with the monopolar electrode probe inserted within the root canal while an electric field is generated as a result of the difference in electrical potential of the monopolar electrode probe and the periodontium.

FIG. 2 is a perspective view of a patient's teeth in which an electric field disinfection apparatus 150 is being used to provide for electric field disinfection of the root canal(s) 102 of tooth 100. FIG. 3 is a cross-sectional view of the tooth 100 and disinfection apparatus of FIG. 2. Apparatus 150 includes an electrical power source (not shown), a ground electrode 154, and a monopolar electrode probe 156. As seen in FIG. 3, probe 156 is advantageously sized and configured for insertion into root canal 102. It is advantageously elongate and may be needle shaped in some cases. According to one embodiment, the monopolar electrode probe 156 can have a length between about 5 mm and about 30 mm, preferably between about 10 mm and about 25 mm, and more preferably between about 12 mm and about 20 mm. According to one embodiment, the diameter of probe 156 may be less than about 2 mm, preferably between about 0.06 mm and about 1 mm, more preferably between about 0.1 mm and about 1 mm, and most preferably between about 0.25 mm and about 0.75 mm.

Figure 4:
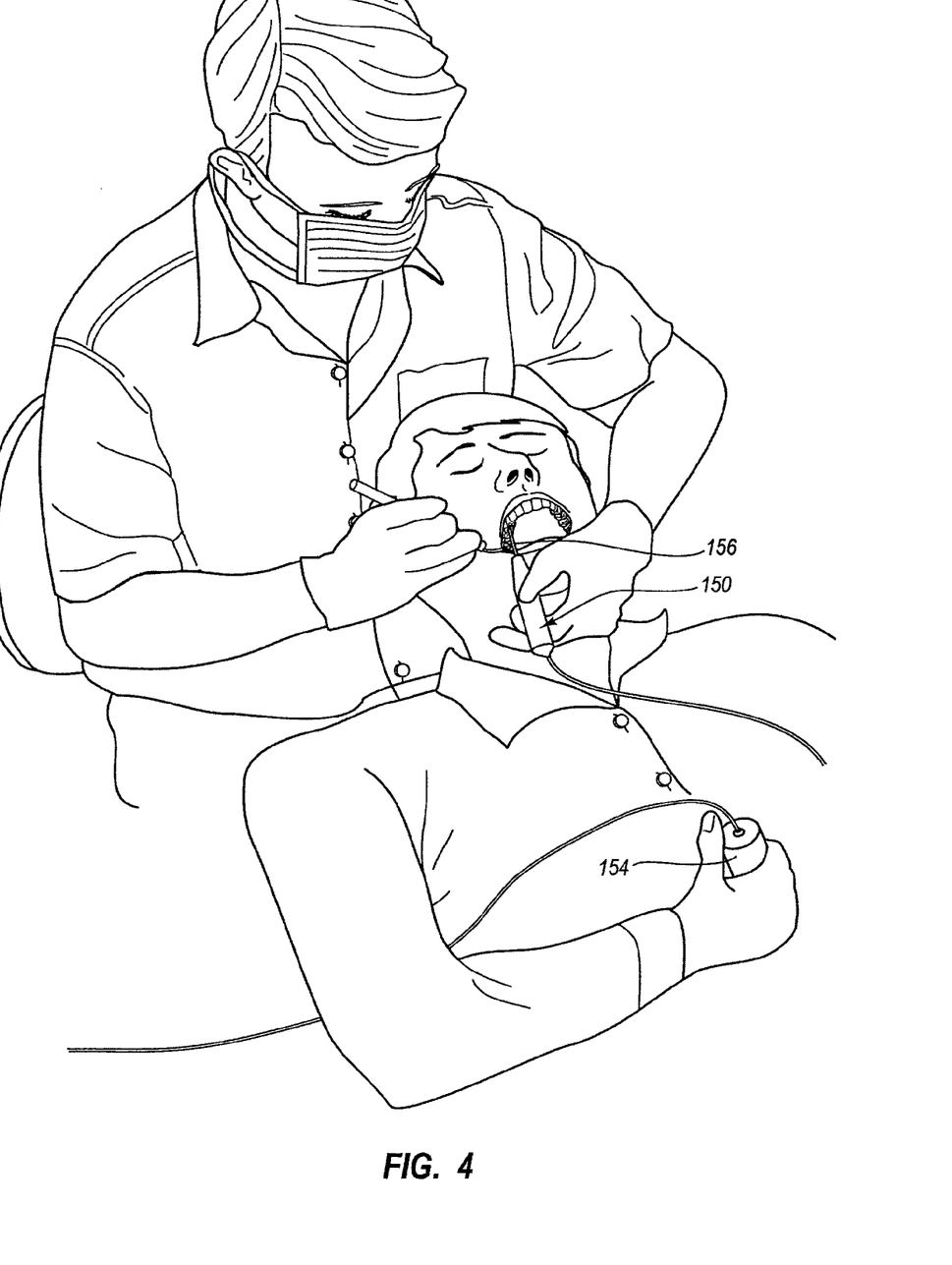
FIG. 4 is a perspective view of a patient in an alternative method similar to that shown in FIG. 2 but in which the ground electrode is held within the hand of the patient.

Ground electrode 154 can be attached to patient 125, for example, to the gingiva 160 adjacent tooth 100 (FIG. 3). Attachment may be accomplished by an adhesive pad surrounding the electrode. Such an adhesive pad aids in holding and electrically connecting the ground electrode 154 to gingival tissue 160. In another embodiment, the ground electrode may be configured to be held within the hand of the patient (FIG. 4). A method in which the ground electrode is held within the patient's hand may reduce the chance of a burn, as an electrode configured to be gripped by or otherwise attached to the hand or other large surface are of that patient's body has substantially greater surface compared to tissues within the patient's mouth. Moreover, if the adhesive pad connected to ground electrode 154 fails to provides adequate adhesion to the moist gingival tissue, a burn may result. In any case, the ground electrode can be electrically connected to the patient by virtually any desired means to provide an electrical "ground" relative to the probe 156 when a voltage differential is applied between ground electrode 154 and probe 156 so as to complete the electrical circuit.

An electrical voltage potential is then applied by the power source between ground electrode 154 and probe 156. The applied voltage is advantageously sufficiently low that virtually no current flows between ground electrode 154 and probe 156. Rather, an electric field is advantageously generated between electrode probe 156 and the periodontum 158, which is electrically connected to ground electrode 154 through the patient's electrically conductive body (e.g., conductive fluids, such as blood). Because of the equipotential characteristics of periodontium 158, it is believed that the electric field only extends between probe 156 and periodontium 158. In other words, the periodontium 158 may act as the ground.

The appropriate applied voltage may depend on the duration of voltage application, whether the voltage is continuous or pulsed, is direct current or alternating current, and if pulsed the nature of the waveform employed (e.g., sine wave, square wave, etc.), as well as the waveform frequency. Voltage may also depend on other variables, for example, on the specific materials and configurations of the ground electrode 154, electrode probe 156, the distance between the electrodes, and the compositional characteristics of water (e.g., aqueous solution 162) or other fluid within the root canal. By way of example, the applied electrical voltage may be between about 1 volt and about 10,000 volts, preferably between about 10 volts and about 10,000 volts, more preferably between about 250 volts and about 2000 volts, and most preferably between about 500 volts and about 1500 volts. In addition to being low enough to prevent significant current flow (e.g., to prevent sparking or arcing, which can result in heat generation and/or tissue damage), the voltage can be sufficiently high to produce an electric field with sufficient strength to eradicate the microbe population that may be present within a root canal preparation or other dental preparation.

The voltage can be applied for a duration sufficient to generate an electric field that is effective in causing electroporation and/or apoptosis and eradication (e.g., at least a 2 log reduction, preferably at least a 3 log reduction, more preferably at least a 4 log reduction) of bacteria (both planktonic and biofilm) within the root canal preparation. According to one embodiment, the voltage may be pulsed during application of the voltage. For example, the total duration of applied voltage (whether pulsed or unpulsed) may be between about 10 nanoseconds and about 30 seconds, preferably between about 0.001 second and about 5 seconds, and more preferably between about 0.01 second and about 4 seconds. Even more preferred durations may be between about 1 second and about 5 seconds, and most preferably may be between about 2 seconds and about 4 seconds.

In the case where the voltage is pulsed, individual pulse durations can typically be between about 1 nanosecond and about 1000 milliseconds (ms), preferably between about 5 nanoseconds and about 500 ms, and more typically between about 1 ms and about 100 ms. Preferred individual pulse duration values may be between about 10 ms and about 1000 ms, more preferably between about 50 ms and about 500 ms, and most preferably between about 100 ms and about 200 ms.

Furthermore, the number of pulses in the case of application of a pulsed voltage may be between about 2 and about 50 million, typically between about 10 and about 3 million, and more typically between about 15 and about 500,000. Most preferred pulse numbers may be between about 2 and about 50, more preferably between about 10 and about 30, and most preferably between about 15 and about 25.

One particular example discovered by the inventor to provide suitable results involves the application of 1000 volts over a duration of about 2.8 seconds, with an individual square wave pulse duration of about 140 ms, a pulse number of about 20 pulses, and a rest time between pulses of about 3 seconds. Preferably, rest times between such pulses can range between about 0.5 second and about 10 seconds, more preferably between about 1 and about 5 seconds.

Such operating parameters have been found by the inventor to be sufficient to result in destruction of bacteria. Although it is believed, according to one theory, that electroporation and/or apoptosis of the bacteria and/or other microbe cell walls may be the mechanism by which killing of the bacteria and other microbes is achieved, the inventor is not bound to this theory, and it is possible that other factors may contribute to or be responsible for the discovered microbe-killing ability of the disclosed methods.

According to one theory, it is believed that the electric field disrupts the integrity of the cell wall, opening pores through the wall and into the interior of the cell. Another theory is that the electric field induces apoptosis, which may trigger an inner biological mechanism of the microbe, resulting in the death of the cell. In any case, the disclosed methods result in killing of the microbes, although the particular mechanism by which the electric field leads to death may not be fully known. According to one theory, an osmotic shock may occur while the membrane breaks down, and the inner environment of the cell is irreversibly damaged. According to another theory, free radicals either generated by the electric field and/or already present within the root canal are able to more easily penetrate through the protective cell wall as a result of cell wall degradation. Under such a theory, any sodium hypochlorite or other residual chemical disinfectant within the root canal should more easily penetrate and kill bacteria cells present in planktonic and/or biofilm formats, leading to an even greater log reduction of the microbial population and a synergistic effect between the electric field and chemical disinfectant. In the case where the method involves application of short pulses, it is believed that the electric field may not be sufficient to cause cell wall breakdown but rather generates the activation of inner cell mechanisms that lead to apoptosis of the cell. In any case, the method has been found effective in eradicating microbes within a root canal or other dental preparation.

Because of the electric field, the concentration of a chemical disinfectant that may otherwise be required to eradicate the bacteria is considerably lower compared to disinfecting the root canal without generation of an electric field. For example, the inventor has found that essentially or almost zero disinfectant concentration may be sufficient, as electric fields can result in eradication of the bacteria by itself (e.g., to yield at least a 2 log, 3 log, or 4 log reduction). The presence of any added chemical disinfectant may serve to increase the log reduction as compared to applying the electric field by itself (e.g., at least a 3 log reduction, 4 log reduction, or 5 log reduction may be achieved when an electric field is employed simultaneously with chemical disinfection). No matter the actual mechanism, it has been found that exposing the root canal and surrounding lateral voids and structures to an electric field as described above surprisingly and advantageously results in eradication of the microbes present, without any need for chemical disinfection, or when using significantly lower concentrations and/or amounts of chemical disinfectant (e.g., less than about 50%, or less than about 75%, or even less than about 90%).

The electrodes 154 and 156 may be formed of any suitable electrically conductive material. Examples of suitable materials include platinum, gold, silver, copper, aluminum, stainless steel, and other metals and alloys. In one embodiment, the monopolar electrode probe 156 that is inserted within the root canal 102 comprises silver, which may also result in release of silver ions during generation of the electric field within the root canal. Silver ions can exhibit an anti-microbial effect, and such an embodiment may act to further reduce the population of microbes within the root canal during the disinfection procedure.

EXAMPLE 1

Extracted teeth were collected and de-coronated. The root canal systems of each tooth were shaped to achieve a size ISO 25 at the apex. The apices where sealed from outside the tooth with a composite resin to avoid direct flow of current from the apex. Each tooth was tightly enveloped in aluminum foil, and a wire was connected. All samples were included in a transparent resin block, with the free end of the wire out. The periphery surrounding the upper access to the root canal system was sealed with composite. All samples were inoculated repeatedly with a culture of *E. faecalis*. Before treatment, liquid inside the root canal system of all the samples was removed from the root canal using absorbent paper points and then placed in a microcentrifuge tube, diluted and plated for determination of viability and number of colony forming units per mL (cfu/mL).

Each root canal system was filled again with sterile 0.1M saline solution. The ground electrode of the generator was connected to the wire extending out of the resin block, and the probe connected with the active electrode was inserted into the root canal system. Under these conditions, 10 pulses of electrical power were applied using the electrodes. Afterwards, liquid inside the root canal system was removed with from the root canal using absorbent paper points and then placed in a microcentrifuge tube, diluted, and plated for determination of viability and number of cfu/mL.

Each root canal system was lightly shaped with an endodontic file, rinsed with 0.1M sterile saline solution, shaped again, rinsed with sterile saline solution again, and then dried. The purpose of this instrumentation was to eliminate any biofilm presumably present on the interior surface of the root canal due to the long inoculation time of the samples. During this procedure, sterile saline solution irrigation (0.1M) was used to wash out debris. The use of saline solution by itself avoided chemical antibacterial activity. At this point, the dentinal tubules deep within the dentin structure still retained their bacteria biofilm.

Subsequent to drying the canal, a 0.5M EDTA solution was applied for 30 seconds in order to eliminate smear plugs due to the filing or abrading action inside the openings of the dentinal tubules. EDTA is not believed to have any significant antimicrobial effect at the concentration used. Afterwards, the root canal system was rinsed with 0.1M sterile saline solution again. Under these conditions, 10 pulses of electrical power were applied using the electrodes, and afterwards the liquid inside the root canal system was dried with paper points then placed in a microcentrifuge tube, diluted and plated for determination of viability and number of cfu/mL.

After the foregoing steps, the root canal was filled with saline and sterile gate #4 was used to collect shavings of dentin, which were dried with paper points and then placed in a microcentrifuge tube, diluted and plated to determine number of cfu/mL. The outcomes after two sets of 10 pulses and instrumentation was a kill rate of 98.7% (about a 2 log reduction) in the root canal system, and a kill rate of 99.9% (a 3 log reduction) in the dentin shavings. The operating parameters were as shown in Table I below.

TABLE I

| Parameter | Value |
| --- | --- |
| Voltage | 1000 V |
| AC/DC | AC |
| AC Frequency | 315 KHz |
| Number of Pulses | 20 |
| Pulse Duration | 140 ms |
| Total Duration | 2.8 seconds |
| Rest Time between Pulses | 3 seconds |

The foregoing test and outcome show how electric fields can be effective in eradicating an otherwise difficult-to-treat infective condition. Dentin is an example of a tissue that can be very difficult to disinfect due to its tubular microstructure. The interior of a tooth is made of dentin, a substance organized in a multi-tubular structure. Typically, dentinal tubules extend from the root canal to the external surface of the root. The microtubules extend generally perpendicularly to the axis of the canal. Such tubules have a diameter of about 2 microns and, seen from inside the canal, have a generally regular disposition, appearing somewhat like a honeycomb. Dentinal tubules, once colonized by a bacterial biofilm, comprise a biological structure that is nearly impossible to sterilize in vivo. According to current endodontic protocol, it is acceptable to leave an amount of bacteria living inside of the microstructure. Such state of the art methods rely on "entombing" and eventual death of the microbial population over time using endodontic cement rather than complete eradication of the microbes in the first instance. The experiment conducted above shows that the concept of achieving substantially complete eradication by electric field generation is achievable.

The needle probe inserted in the root canal system is an electrode that generates an electric field that has a correspondent in the periodontium that acts as the second (i.e., ground) electrode such that the entirety of the dentin wall can be within the influence of the electric field. This allows killing substantially all of the bacteria residing both within the dentin and the root canal. There are no significant side effects within tissue beyond the periodontium because electric field effects beyond the periodontium are greatly diminished.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for disinfecting a root canal preparation of a patient, comprising:
    electrically connecting a ground electrode to a body of the patient so as to provide an electrical ground;
    inserting a monopolar probe into a root canal preparation of a tooth of the patient; and
    applying an electrical voltage to the monopolar probe inserted within the root canal preparation so as to produce an electric field within the root canal preparation, the electric field interacting with and killing microbes within the root canal preparation without damage to or substantial heating of tissue or material within the root canal preparation.

2. A method as recited in claim 1, wherein the root canal preparation contains an aqueous conducting fluid when the electrical voltage is applied.

3. A method as recited in claim 2, wherein the aqueous conducting fluid does not include a chemical disinfectant such that the electric field kills the microbes without assistance of a chemical disinfectant.

4. A method as recited in claim 2, wherein the aqueous conducting fluid comprises a chemical disinfectant that assists the electric field in killing the microbes.

5. A method as recited in claim 4, wherein the chemical disinfectant comprises aqueous sodium hypochlorite.

6. A method as recited in claim 1, wherein applying an electrical voltage comprises applying an electrical voltage in a range of about 1 volt to about 10,000 volts.

7. A method as recited in claim 1, wherein applying an electrical voltage comprises applying an electrical voltage in a range of about 250 volts to about 2000 volts.

8. A method as recited in claim 1, wherein applying an electrical voltage comprises applying an electrical voltage in a range of about 500 volts to about 1500 volts.

9. A method as recited in claim 1, wherein applying an electrical voltage comprises applying an electrical voltage over a time duration in a range of about 10 nanoseconds to about 30 seconds.

10. A method as recited in claim 1, wherein applying an electrical voltage comprises applying an electrical voltage over a time duration in a range of about 0.001 second to about 5 seconds.

11. A method as recited in claim 1, wherein applying an electrical voltage comprises applying an electrical voltage over a time duration in a range of about 0.01 second to about 4 seconds.

12. A method as recited in claim 1, wherein applying an electrical voltage comprises applying an electrical voltage that is pulsed, wherein individual pulses of the electric voltage have a time duration in a range of about 1 nanosecond to about 1000 milliseconds.

13. A method as recited in claim 12, wherein applying an electrical voltage comprises applying a number of individual pulses in a range of 2 to about 50 million.

14. A method as recited in claim 12, wherein applying an electrical voltage comprises applying a number of individual pulses in a range of about 10 to about 3 million.

15. A method as recited in claim 12, wherein applying an electrical voltage comprises applying a number of individual pulses in a range of about 15 to about 500,000.

16. A method as recited in claim 12, wherein applying an electrical voltage comprises providing a rest time between individual pulses in a range of about 1 second to about 5 seconds.

17. A method as recited in claim 12, wherein there is a rest time between individual pulses in which the rest time is in a range of about 0.5 second to about 10 seconds.

18. A method as recited in claim 12, wherein there is a rest time between individual pulses in which the rest time is in a range of about 1 second to about 5 seconds.

19. A method as recited in claim 1, wherein applying an electrical voltage comprises applying an electrical voltage that is pulsed, wherein individual pulses of the electric voltage have a time duration in a range of about 5 nanoseconds to about 500 milliseconds.

20. A method as recited in claim 1, wherein applying an electrical voltage comprises applying an electrical voltage that is pulsed, wherein individual pulses of the electric voltage have a time duration in a range of about 1 millisecond to about 200 milliseconds.

21. A method as recited in claim 1, wherein applying an electrical voltage results in virtually no electrical current flow between the monopolar probe inserted within the root canal preparation and the ground electrode.

22. A method as recited in claim 1, wherein the monopolar probe inserted within the root canal preparation comprises silver.

23. A method as recited in claim 1, wherein the ground electrode further comprises an adhesive pad for holding the ground electrode to gingival tissue.

24. A method as recited in claim 1, wherein the monopolar probe has a length in a range of about 12 mm to about 20 mm.

25. A method as recited in claim 1, wherein the monopolar probe has a diameter in a range of about 0.06 mm to about 1 mm.

26. A method as recited in claim 1, the electric field interacting with and killing microbes by electroporation and disruption of microbe cell walls.

27. A method as recited in claim 1, the electric field interacting with and killing microbes by microbe apoptosis causing an inner biological mechanism that results in killing of the microbes.

28. A method as recited in claim 1, the method resulting in at least a 2 log reduction of microbes within the root canal preparation.

29. A method as recited in claim 1, the method resulting in at least a 3 log reduction of microbes within the root canal preparation.

30. A method as recited in claim 1, the method resulting in at least a 4 log reduction of microbes within the root canal preparation.

31. A method as recited in claim 1, the electric field heating surrounding dental tissue by less than about 10° C.

32. A method as recited in claim 1, the electric field heating surrounding dental tissue by less than about 5° C.

33. A method as recited in claim 1, the electric field heating surrounding dental tissue by less than about 2° C.

34. A method for disinfecting a root canal preparation of a patient, comprising:
    providing a root canal preparation of the patient's tooth that contains an electrically conductive fluid;
    electrically connecting a ground electrode to gingival tissue of the patient so as to provide an electrical ground;
    inserting a monopolar probe into a root canal preparation of a tooth of the patient; and
    applying an electrical voltage to the monopolar probe inserted within the root canal preparation so as to produce an electric field within the root canal preparation, the electric field interacting with and killing microbes within the root canal preparation without damage to or substantial heating of tissue or material within the root canal preparation, the electric field causing at least one of disruption of microbe cell walls or an inner biological mechanism of microbes that results in killing of the microbes.

35. An apparatus for use in disinfecting a root canal preparation of a patient, comprising:
- a ground electrode configured for attachment to a body of a patient so as to provide an electrical ground;
- a monopolar probe sized and configured for insertion into a root canal preparation of a tooth of a patient; and
- means for applying an electrical voltage to the monopolar probe when inserted within a root canal preparation so as to produce an electric field within the root canal preparation that interacts with and kills microbes within the root canal preparation by at least one of disruption of microbe cell walls or an inner biological mechanism of microbes, the means for applying an electrical voltage being configured to apply an electrical voltage which produces an electric field that kills microbes when the monopolar probe is inserted within a root canal preparation without damage to or heating of tissue or material within the root canal preparation and without heating adjacent dentin by more than about 10° C.

* * * * *